(12) United States Patent
Barron et al.

(10) Patent No.: US 8,940,331 B2
(45) Date of Patent: Jan. 27, 2015

(54) HYDROGELS, METHODS OF MAKING HYDROGELS, METHODS OF USING HYDROGELS, AND METHODS OF ISOLATING, TRAPPING, ATTRACTING, AND/OR KILLING CANCER CELLS

(75) Inventors: Annelise E. Barron, Palo Alto, CA (US); Kavi P. Mehta, Milwaukee, WI (US); Vinod Srinivasan, San Diego, CA (US); Nicolynn E. Davis, Palo Alto, CA (US); Wei Huang, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1015 days.

(21) Appl. No.: 12/624,043

(22) Filed: Nov. 23, 2009

(65) Prior Publication Data
US 2010/0159008 A1 Jun. 24, 2010

Related U.S. Application Data

(60) Provisional application No. 61/117,100, filed on Nov. 22, 2008.

(51) Int. Cl.
*A61K 9/14* (2006.01)
*C12P 21/00* (2006.01)
*C07K 14/00* (2006.01)
*A61K 38/00* (2006.01)

(52) U.S. Cl.
CPC ............... *C12P 21/00* (2013.01); *C07K 14/001* (2013.01); *A61K 38/00* (2013.01)
USPC .......................................................... 424/484

(58) Field of Classification Search
None
See application file for complete search history.

(56) References Cited

U.S. PATENT DOCUMENTS 7,642,239 B2 * 1/2010 Taylor et al. .................... 514/1.1
2009/0053141 A1 * 2/2009 Sulzer et al. ................. 424/9.34

OTHER PUBLICATIONS

Moreau et al ("Tissue-Engineered Bone Serves as a Target for Metastasis of Human Breast Cancer in a Mouse Model," Cancer Res 2007;67: (21). Nov. 1, 2007) [Moreau].*

* cited by examiner

*Primary Examiner* — Suzanne Ziska
(74) *Attorney, Agent, or Firm* — Thomas|Horstemeyer, LLP

(57) ABSTRACT

Embodiments of the present disclosure provide for hydrogels, methods of making hydrogels, methods of using hydrogels, methods of isolating, trapping, attracting, and/or killing cancer cells, and the like.

39 Claims, 1 Drawing Sheet

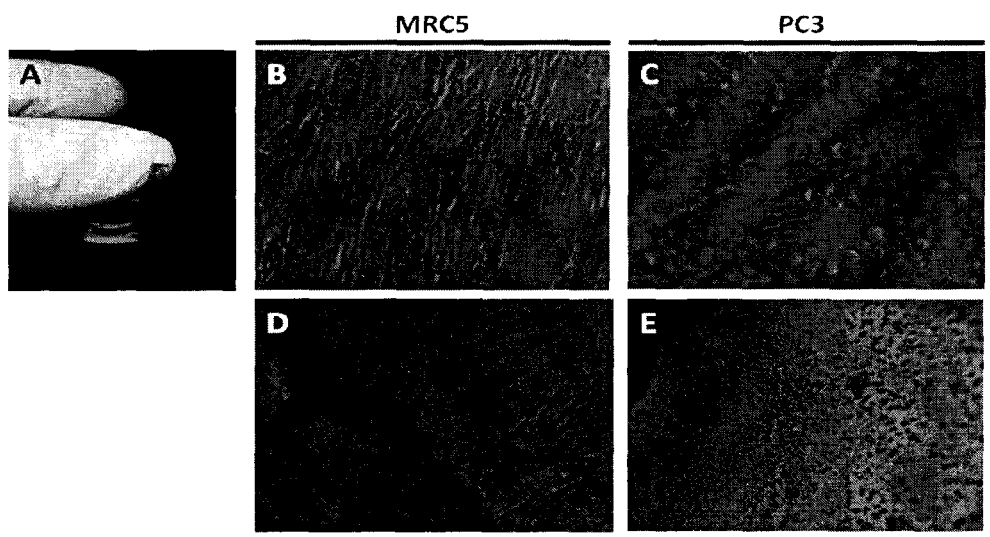

SEQUENCE LISTING

```
<160> NUMBER OF SEQ ID NOS: 16

<210> SEQ ID NO 1
<211> LENGTH: 13
<212> TYPE: PRT
<213> ORGANISM: Artificial Sequence
<220> FEATURE:
<223> OTHER INFORMATION: Chemically synthesized Q substrate

<400> SEQUENCE: 1

Gly Gln Gln Gln Leu Gly Gly Ala Gly Thr Gly Ser Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Chemically synthesized Q substrate

<400> SEQUENCE: 2

Gly Ala Gly Gln Gly Glu Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Chemically synthesized Q substrate
```

-continued

<400> SEQUENCE: 3

Gly Leu Gln Gln Gln
1               5

<210> SEQ ID NO 4
<211> LENGTH: 5
<212> TYPE: PRT
<213> ORGANISM: Artificial Sequence
<220> FEATURE:
<223> OTHER INFORMATION: Chemically synthesized Q substrate

<400> SEQUENCE: 4

Leu Gln Gln Gln Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Chemically synthesized Q substrate

<400> SEQUENCE: 5

Gly Leu Gln Gln Gln Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Chemically synthesized K substrate

<400> SEQUENCE: 6

Gly Lys Gly Thr Gly Ala
1               5

<210> SEQ ID NO 7
<211> LENGTH: 8
<212> TYPE: PRT
<213> ORGANISM: Artificial Sequence
<220> FEATURE:
<223> OTHER INFORMATION: Chemically synthesized K substrate

<400> SEQUENCE: 7

Gly Lys Gly Ser Gly Lys Gly Ala
1               5

<210> SEQ ID NO 8
<211> LENGTH: 8
<212> TYPE: PRT
<213> ORGANISM: Artificial Sequence
<220> FEATURE:
<223> OTHER INFORMATION: Chemically synthesized K substrate

<400> SEQUENCE: 8

Gly Lys Ala Gly Thr Gly Ser Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Chemically synthesized substrate for MMP 2

```
<400> SEQUENCE: 9

Gly Pro Gln Gly Ile Trp Gly Gln
1               5

<210> SEQ ID NO 10
<211> LENGTH: 19
<212> TYPE: PRT
<213> ORGANISM: Artificial Sequence
<220> FEATURE:
<223> OTHER INFORMATION: Chemically synthesized Cell adhesion signal2

<400> SEQUENCE: 10

Ile Thr Val Tyr Ala Val Thr Gly Arg Gly Asp Ser Pro Ala Ser Ser
1               5                   10                  15

Arg Pro Ile

<210> SEQ ID NO 11
<211> LENGTH: 19
<212> TYPE: PRT
<213> ORGANISM: Artificial Sequence
<220> FEATURE:
<223> OTHER INFORMATION: Chemically synthesized scrambled cell adhesion
      signal

<400> SEQUENCE: 11

Ile Thr Val Tyr Ala Val Thr Gly Arg Asp Gly Ser Pro Ala Ser Ser
1               5                   10                  15

Arg Pro Ile

<210> SEQ ID NO 12
<211> LENGTH: 17
<212> TYPE: PRT
<213> ORGANISM: Artificial Sequence
<220> FEATURE:
<223> OTHER INFORMATION: Chemically synthesized heparin binding domain:
      higher affinity

<400> SEQUENCE: 12

Gly Arg Arg Arg Arg Ala Arg Arg Arg Ala Arg Arg Arg Arg Ala
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: Chemically synthesized heparin binding domain:
      lower affinity

<400> SEQUENCE: 13

Gly Arg Pro Arg Ala Arg Ala Arg Ala Arg Ala Arg Asp Gln Thr Arg
1               5                   10                  15

Gly

<210> SEQ ID NO 14
<211> LENGTH: 5
<212> TYPE: PRT
<213> ORGANISM: Artificial Sequence
<220> FEATURE:
<223> OTHER INFORMATION: Chemically synthesized adhesion substrate
      sequence

<400> SEQUENCE: 14
```

```
Pro His Ser Arg Asn
1               5

<210> SEQ ID NO 15
<211> LENGTH: 6
<212> TYPE: PRT
<213> ORGANISM: Artificial Sequence
<220> FEATURE:
<223> OTHER INFORMATION: Chemically synthesized adhesion substrate
      sequence

<400> SEQUENCE: 15

Lys Gln Ala Gly Asp Val
1               5

<210> SEQ ID NO 16
<211> LENGTH: 5
<212> TYPE: PRT
<213> ORGANISM: Artificial Sequence
<220> FEATURE:
<223> OTHER INFORMATION: Chemically synthesized adhesion substrate
      sequence

<400> SEQUENCE: 16

Tyr Ile Gly Ser Arg
1               5
```

HYDROGELS, METHODS OF MAKING HYDROGELS, METHODS OF USING HYDROGELS, AND METHODS OF ISOLATING, TRAPPING, ATTRACTING, AND/OR KILLING CANCER CELLS

CROSS-REFERENCE TO RELATED APPLICATION

This application claims priority to U.S. provisional applications entitled, "IMPLANTED OR IN SITU-FORMED HYDROGELS THAT ATTRACT AND SEQUESTER MIGRATORY CANCER CELLS AND KILL THEM BY THE CONTROLLED RELEASE OF CATIONIC AMPHIPATHIC PEPTOIDS, METHODS OF MAKING AND METHODS OF USING HYDROGELS," having Ser. No. 61/117,100 filed on Nov. 22, 2008, which is entirely incorporated herein by reference.

FEDERAL SPONSORSHIP

This invention was made, in part, with Government support under Contract/Grant No. 5 R01 EB003806, awarded by the National Institutes of Health, National Institute of Biomedical Imaging and Bioengineering. The Government has certain rights in this invention.

BACKGROUND

Current cancer treatment options typically involve a combination of invasive surgery to excise cancerous tissue that can be detected, followed by radiotherapy and chemotherapy. The latter two treatments, while causing substantial tissue damage and illness, are deployed as tools to kill any cancer cells that remain and which either could not be detected or could not be removed. These methods are not very effective in reducing cancer recurrence, especially in patients whose cancers are detected at late stages. If we consider cases in which cancer is detected at an early stage, so that cancer cells have not yet been disseminated from the primary site, surgery may leave residual cancer cells in the periphery of the tumor site and/or can cause tumor fragmentation, which can increase the chances of recurrence. In additional, natural wound healing processes initiated at the surgical site flood the area with growth factors, and this can stimulate enhanced proliferation or migration of any residual cancer cells (which is one reason that radiation is generally applied locally, after surgery). In breast cancer, if tumor formation recurs, it tends to be in the lungs or in lymph nodes near the breast tissue. The major source of this type of metastasis is residual cancerous cells left by invasive tumor removal procedures, such as a lumpectomy, even with the application of combined radio- and chemotherapy treatments, or by recurring cancerous cells at the primary tumor site, which then become metastatic, by migrating into lymphatic channels or blood vessels. Besides the common case of cancer recurrence, patients who are treated according to the most common disease management protocol often suffer from a variety of severe side effects of current treatments. Chemotherapeutics and gamma irradiation treatments often lack specificity and damage healthy tissue in the process, which leads to discomfort or pain that exhausts patients, depresses their immune systems, and begin tissue remodeling processes that have long-term negative health consequences (e.g., edema, scarring, or lung damage eventually leading to impaired breathing).

At this time, there is a clear need to provide alternative approaches to the treatment of cancer and other diseases involving the dissemination of cells with pathological characteristics.

SUMMARY

Embodiments of the present disclosure provide for hydrogel, methods of making hydrogels, methods of using hydrogels, methods of isolating pathogenic cells such as cancer cells, and the like.

An embodiment includes a hydrogel, among others, that includes a Q block including a Q substrate including at least one glutamine group; a K block including a K substrate including at least one lysine group; and a biocompatibility substrate or a biocompatibility substance, wherein the Q block and the K block are crosslinked to one another via one or more glutamine groups of the Q block and one or more of the lysine groups of the K block; wherein one or both of the Q block and the K block include a random coil protein substrate.

An embodiment includes a hydrogel, among others, that includes a reaction product including a biocompatibility substrate, wherein the reaction product is formed from a Q block and a K block in the presence of an enzymatic cross-linking agent, wherein a Q block includes a Q substrate including at least one glutamine group and the K block includes a K substrate including at least one lysine group, wherein one or both of the Q block and the K block include a random coil substrate; wherein the Q block and the K block are cross-linked to one another via one or more glutamine groups of the Q block and one or more of the lysine groups of the K block, wherein the reaction product is a random coil polypeptide polymer substrate.

An embodiment includes a method of making a hydrogel, among others, that includes mixing a Q block and a K block in the presence of an enzymatic cross-linking agent, wherein a Q block includes a Q substrate including at least one glutamine group and the K block includes a K substrate including at least one lysine group, wherein one or both of the Q block and the K block include a random coil substrate; enzymatically cross-linking the Q block and the K block to form a random coil polypeptide polymer substrate having a biocompatibility substrate, wherein the Q block and the K block are cross-linked to one another via one or more glutamine groups of the Q block and one or more of the lysine groups of the K block; and forming a hydrogel from the random coil polypeptide polymer substrate.

An embodiment includes a method of isolating a cancerous human cell from surrounding non-cancerous tissue, among others, that includes disposing the hydrogel in a subject, wherein the hydrogel is a random coil polypeptide polymer substrate including: a Q block including a Q substrate including at least one glutamine group; a K block including a K substrate including at least one lysine group; and a biocompatibility substrate, wherein the Q block and the K block are cross-linked to one another via one or more glutamine groups of the Q block and one or more of the lysine groups of the K block; wherein one or both of the Q block and the K block include a random coil substrate; wherein the hydrogel includes a bioactive substance selected from the group consisting of: an agent, a bioactive substrate, and a combination thereof, wherein a cancerous human cell has an affinity for the bioactive substance; and allowing the cancerous human cells to interact with the hydrogel and become disposed in the hydrogel.

An embodiment includes a method of using a hydrogel, among others, that includes disposing the hydrogel in a subject, wherein the hydrogel is a random coil polypeptide polymer substrate including: a Q block including a Q substrate including at least one glutamine group; a K block including a K substrate including at least one lysine group; and a biocompatibility substrate, wherein the Q block and the K block are cross-linked to one another via one or more glutamine groups of the Q block and one or more of the lysine groups of the K block; wherein one or both of the Q block and the K block include a random coil substrate; wherein the hydrogel includes a bioactive substance selected from the group consisting of: an agent, a bioactive substrate, and a combination thereof, wherein pathogenic cells have an affinity for the bioactive substance; and allowing the pathogenic cells to interact with the hydrogel.

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A-1E illustrates an in vitro invasion assay. FIG. 1A illustrates a transwell chamber with a filter membrane on the bottom, coated with a layer of 5% (wt) protein hydrogel. FIGS. 1B to 1C) illustrates a cell attachment observed 12 hours after seeding. FIGS. 1D to 1E illustrate that after 5 days of cell seeding the filter membranes beneath the hydrogels were fixed and stained. FIGS. 1B and 1D are MRC5 cancer cells. FIGS. 1C and 1E are PC3 cancer cells.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of biochemistry, synthetic organic chemistry, biology, molecular biology, recombinant DNA techniques, pharmacology, imaging, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

DEFINITIONS

In describing and claiming the disclosed subject matter, the following terminology will be used in accordance with the definitions set forth below.

The term "polymer" means any compound that is made up of two or more monomeric units covalently bonded to each other, where the monomeric units may be the same or different, such that the polymer may be a homopolymer or a heteropolymer. Representative polymers include polyamides, such as polypeptides, poly-N-substituted glycines (polypeptoids), polysaccharides, polyethylene glycol or polyethylene oxide, plastics (e.g., poly-L-lactic acid, poly-L-glutamic acid and co-polymers thereof), nucleic acids and the like, where the polymers may be naturally occurring, non-naturally occurring, or synthetic.

The term "polypeptides" includes proteins and fragments thereof. Polypeptides are disclosed herein as amino acid residue (or monomer) sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids or post-translationally modified amino acids such as hydroxylated amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, selenomethionine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methylglycine or other N-substituted glycines, beta-amino acids, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotide encompasses the terms "nucleic acid," "nucleic acid sequence," or "oligonucleotide" as defined above. Another potential class of compounds that could be included is the peptide nucleic acids, or PNAs, which have a polyamide backbone with appended RNA- or DNA-like bases.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

Various chemically or biologically synthesized conjugates of the abovementioned elements, including DNA-polymer, RNA-polymer, polypeptide-polymer or protein-polymer conjugates may comprise an element of an embodiment of the present disclosure. Protein-polypeptide, protein-polypeptoid, polypeptide-DNA or polypeptide-RNA conjugates may also be included elements.

As used herein, the terms "treatment", "treating", and "treat" are defined as acting upon a disease (e.g., cancer), disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass providing a pharmacologic effect, even in the absence of a disease or condition. For example, "treatment" encompasses providing for enhanced or desirable effects in the subject (e.g., reduction of pathogen load, reduction of disease symptoms, the extension of a period of a patient's apparent, functional health, etc.).

As used herein, the terms "prophylactically treat" or "prophylactically treating" refers completely or partially preventing a disease or symptom thereof and/or may be therapeutic in terms of a partial or complete cure for a disease and/or adverse effect attributable to the disease.

The term "attached" or the phrases "interacts with" and "associated with" refers to a stable physical, biological, biochemical, and/or chemical association. In general, association can be chemical bonding (e.g., covalently or ionically), a biological interaction, a biochemical interaction, and in some instances a physical interaction. The association can be a covalent bond, a non-covalent bond, an ionic bond, a metal ion chelation interaction, as well as moieties being linked through interactions such as, but not limited to, hydrophobic interactions, hydrophilic interactions such as hydrogel bonding, charge-charge interactions, π-stacking interactions, combinations thereof, and like interactions.

The term "cancer", as used herein, shall be given its ordinary meaning, as a general term for diseases in which abnormal cells divide without control and form cancer or neoplastic cells or tissues. The term cancer can include cancer cells and/or precancerous cells. In particular, and in the context of the embodiments of the present disclosure, cancer refers to angiogenesis-related cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor may be formed. Generally, a solid tumor is an abnormal mass of tissue that usually does not contain cysts or liquid areas (although some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult. Benign tumors have less of a tendency to invade and are less likely to metastasize.

Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

As used herein "administration" refers to introducing a compound into a subject. The preferred route of administration is through a surgical procedure, whether performed conventionally or by minimally invasive approaches.

As used herein, the term "subject", "host", or "organism" includes humans and mammals (e.g., cats, dogs, horses, etc.). Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

The term "substrate" can in some instances mean an amino acid sequence upon which an enzyme can act. However, the use of the term "substrate" does not require that an enzyme act upon the substrate. In some instances the term "substrate" may simple bond or attach to another substrate without an enzyme action. The meaning of the term substrate will be apparent upon its use herein.

General Discussion

Embodiments of the present disclosure include hydrogels, methods of making hydrogels, methods of using hydrogels, methods of isolating, trapping, attracting, and/or killing cancer cells, and the like.

In general, embodiments of the present disclosure provide for the creation of hydrogel-based implants with therapeutic applications in the management of diseases involving the potential spread of pathological, migratory cells, such as cancer.

One exemplary therapeutic hydrogel implant, among others, is a protein-based hydrogel (pre-formed and implanted via standard surgical approaches at the site of tumor excision, or alternatively, formed from a liquid pre-cursor solution by in situ gelation after delivery by minimally invasive means) which, after being placed in a tissue defect resulting from tumor excision surgery, provides for the timed release of certain chemokines, growth factors, and/or growth factor mimetics into local tissue, which serve to arrest or attract chemokine-sensitive cancer cells that have pathologically high numbers of cell surface receptors for said growth factors. Arresting or attracting residual cancer cells remaining after surgery can effectively prevent them from migrating into lymphatic or blood circulation, reducing, limiting, or eliminating metastasis in some patients whose disease is diagnosed while the first tumor tissue remains localized in the site of its initial discovery Hydrogels have been widely developed and used within research laboratories as cell culture and tissue regeneration platforms and as drug delivery devices. Hydrogels can be created, in principle, with material properties that closely match the mechanical properties of the surrounding tissues, with their porosity and conjugated adhesion and other biorecognition or gel crosslinking molecules further optimized to facilitate rapid cell infiltration, with or without proteolytic cleavage of the hydrogel polymers by the invading cells.

In contrast to the typical use of hydrogels, embodiments of the present disclosure use hydrogels in an unconventional manner, which has the advantage of being essentially orthogonal or potentially complementary to conventional approaches to treating diseases such as cancer (e.g., the term cancer can refer to cancer cells, precancerous cells, and tumor or tumor cells). In general, embodiments of the present disclosure can be used to slow the outward-directed migration, attract, retain, sequester, trap, and/or kill cancer cells such as cancer cells. In particular, embodiments of the present disclosure can be used alone or to supplement traditional surgical, chemotherapy, and radiotherapy treatments to slow, reduce, or prevent cancer metastasis and tumor recurrence.

Complications of cancer metastasis and the infiltration of residual cancer cells (that remain after tumor removal surgery) into other tissues, which can compromise healthy tissue functions, are a leading cause of cancer morbidity and mortality, and lead to 90% of all cancer deaths. Cancer metastasis occurs when malignant cells migrate in an outward direction away from or become separated or broken off from a primary tumor and travel to a secondary, remote location within the body to establish a new tumor site. Specifically, the steps in metastasis may include the intravasation of tumor cells, penetration of cancer or malignant cells into blood or lymphatic vessels and entry into circulation, arrest in distant organs, extravasation from the blood stream into a tissue site such as bone marrow or lung, and finally cell division and tumor growth. The location of secondary (metastatic) tumors is not random; metastatic cells often home to specific areas. There are three proposed types of homing mechanisms, which are not necessarily mutually exclusive: (1) selective growth, where tumor cells grow in organs that have favorable growth factors and/or offer a particular extracellular matrix (ECM) environment; (2) selective adhesion to sites of organ homing; and, (3) selective chemotaxis to an organ that releases particular soluble attraction factors. These mechanisms involve, at a minimum, the interaction of cancer cells with growth factors and other signaling molecules, chemokines, cell-cell adhesion molecules (cadherins, integrins) and ECM proteases (matrix metalloproteinases). Embodiments of the present disclosure can use these mechanisms to attract and/or slow, immobilize, and concentrate cancer cells.

Metastatic cells often are highly migratory relative to normal cells, with well-documented enhanced responsiveness to certain growth factors, including SDF-1, BMP-2, EGF, and IGF-1, etc. There are tremendous amounts of findings that genes related with cell migrations and genes encoding receptors for some growth factors are up-regulated in metastatic cells. Embodiments of the implanted hydrogel may limit metastasis by one or more of the following: (1) releasing these potent signaling moieties (growth factors such as SDF-1 or EGF) to attract migratory cancer cells; (2) presenting adhesion moieties within or upon the hydrogel implant, so that cancer cells actively migrate into the hydrogel, (3) patterning a higher density of integral or adhesion peptides near the core of the hydrogel, trapping individual cancer cells via the formation of a high density of focal adhesions, and/or (4) releasing chemotherapeutic drugs, polypeptides, or polypeptoids that are able to bind to, penetrate, and kill cancer cells with some specificity relative to normal cells, within a small radius of the hydrogel core. With low to no systemic toxicity, certain embodiments of the hydrogel could be used to reduce the likelihood of cancer metastasis. Such a hydrogel implant could be used on its own, or as a complement to other chemotherapeutic or radiation treatments.

Embodiments of the present disclosure include an implantable hydrogel that selectively attracts cancer (malignant cancer) cells by providing the appropriate adhesion molecules and chemoattracting signals, which can be either be associated with (e.g., tethered to) the hydrogel, or which could be released from the hydrogel to form a local concentration gradient to minimize distant spreading of metastatic cancer cells. In addition, this system could be loaded with nano- or microparticles formed from a plastic or hydrogel material, which release cancer cell-killing compounds, to kill sequestered cancer cells. In this system, a certain selectivity of killing for cancer as opposed to normal mammalian cells can be achieved either by the inherent cancer specificity of the drug itself, or by the highly localized nature of the delivery of the chemotherapeutic drug. By initially attracting and sequestering cancer cells into a localized system, the design of the hydrogel can be employed as a preparation that could boost the efficacy of other therapies, allowing the to be applied in a more targeted manner, such as radiotherapy.

Current therapeutic approaches, such as radio- or chemotherapy, typically have significant negative impacts on patient health, because they lack specificity towards cancer cells and require repeated administration. Embodiments of the present disclosure offer a new and more specific approach that includes the localized implantation or delivery of a functionalized hydrogel system (referred to herein as the "hydrogel") to the primary tumor site, after tumor excision. In certain embodiments, a functionalized hydrogel implant may be placed near to, or might partially or totally surround, a tumor that remains in situ, so that the tumor will necrose in place over time. To reduce systemic toxicities of this design, the targeting effects of the hydrogel can be achieved in a number of ways. The first takes advantage of the high motility and sensitivity of cancer cells towards chemoattractants (e.g., growth factors such as SDF-1 or EGF) through hyper-expressed cell surface receptors, compared to the more limited migration and infiltration ability of normal tissue cells; while a second is based on the release of cytotoxic substrates or agents that can kill cancer cells with a useful level of selectivity, relative to current chemotherapeutic drugs.

As mentioned above, embodiments of the present disclosure include hydrogels that can be used to treat disease such as cancer (e.g., prostate cancer, breast cancer, and the like) which will slow, limit, and/or prevent metastasis in early-diagnosed disease. Embodiments of the present disclosure include an implantable hydrogel that is formed in the space from which a tumor was removed, which attracts, sequesters, traps, and/or kills migratory cancer cells.

Embodiments of the present disclosure can be used to provide a localized and reduced-toxicity approach to reducing or preventing cancer dissemination, metastasis, and/or recurrence after surgical removal of a tumor. Embodiments of the present disclosure can be implanted or in situ-formed and can function to selectively attract, trap, and in some embodiments also kill residual cancer cells for extended periods of time, thereby slowing, reducing, limiting, or preventing tumor recurrence and metastasis with little to no systemic toxicity. The implanted hydrogel can be formed and/or implanted at a void in the tissue which is the site of tumor excision, ideally at the time of surgery or soon after, and can be modified to display bioactive adhesion molecules and to release chemotactic agents to which cancer cells may respond. The adhesion moieties (chemokines) could be most effective if presented and/or released in a radically inward increasing concentration gradient (mobile or immobile) to stimulate cancer cell migration towards and then within the hydrogel towards its core.

In one embodiment, this hydrogel could have a higher density of adhesion moieties at its center, which would trap cancer cells in localities near the hydrogel core. This core, in turn, could be engineered to release cancer cell-specific killing or subduing agents, for instance from dissolving polylactic-glycolic acid or silk-based nano- or microparticles. This approach differs from traditional cancer treatment strategies by exploiting the inherently migratory tendency of metastatic cancer cells, as well as their high affinity for and enhanced sensitivity to and migration towards specific growth factors such as SDF-1, EGF, IGF-1, BMP-2, etc., depending on the particular type of cancer cell. Such growth factors would also promote the optimal healing of the surgical site, in addition to performing a cancer cell-attracting function.

Embodiments of the hydrogel can have a modular design, providing an inherent flexibility of design and formulation to enable quick system re-design and evolution, either to tailor the gel to be efficacious for a particular type of cancer or even for particular subjects being treated for cancer, and to allow the incorporation of newly discovered compounds that can enhance system performance, for instance by stimulating directed cancer cell migration into the gel, or cell adhesion within the hydrogel, or by accomplishing specific, systemically non-toxic cancer cell killing.

In other embodiments, the hydrogel can provide further benefit to subjects via implantation, e.g., by being designed in such a way as to provide for a controlled release of analgesics or opiates to reduce the subject's local discomfort after surgery, and/or the release of antibiotics to prevent or treat post-surgical infections.

Embodiments of the hydrogels can be specifically designed via tunable material properties (e.g., gel stiffness, porosity, and degradation rate). Selection of the polypeptides that make up the hydrogel and the degree of cross-linking of the polypeptides can be used to control the material characteristics of the hydrogel. In addition, the hydrogel can be designed to control the concentration of presented bioactive substrates (e.g., adhesion substrates, protease substrates, and the like).

Embodiments of the present disclosure can be developed based on hydrogels that are formed from recombinant "protein polymers", i.e., long proteins that have repetitive amino acid sequences. In addition, the hydrogel can be a hybrid synthetic material incorporating synthetic polymers such as poly(ethylene glycol) in addition to biosynthetically derived, repetitive proteins. Embodiments of the hydrogel can include high-molar mass protein polymers produced by genetic engineering and bacterial expression, which can be purified fully (to remove all traces of bacterial cell wall contamination) and then can be enzymatically crosslinked into hydrogels that have viscoelastic properties. The biosynthesis of protein polymers in E. Coli, via the expression of novel, recombinant genes, allows for precisely controlled protein length (monodispersity) and for specifically tailored amino acid sequences (controlled reactivity) which allows for highly tunable material properties.

As described in more detail below, the hydrogel can be formed from protein polymers that can be crosslinked into a hydrogel using a chemical, physical, and/or biological crosslinking agent (e.g., enzyme tissue transglutaminase), which forms a stable bond between lysine and glutamine residues present in the corresponding polypeptides or proteins. In an embodiment, enzymatically crosslinked hydrogels can be formed within minutes. Proteins that display repetitive lysine residues ("K block protein polymers") also can be cross-linked using chemical crosslinkers, either alone or in combination with hydrogel stabilization by trans-glutaminase crosslinking. In addition, protein polymer hydrogels can be composed of self-assembling domains that contain self-assembling, $\alpha$-helical coiled-coil regions as a way to control hydrogel stiffness, or alternatively, self-assembling $\beta$-sheet regions that accomplish a similar function of providing stabilization of the hydrogel in vitro or in vivo. The length of the self-assembling domains and their association state (i.e., number of bundled helices or associated chains held together by hydrogen bonding) can be varied and is anticipated to strongly affect the mechanical properties of the hydrogel. Detailed aspects of the protein polymer hydrogel design will determine its material properties, network structure, and gel pore size. Biosynthetic material synthesis can also allow for fine-tuning of the hydrogel's degradation rate in vivo and density of grafted-on bioactive display moieties.

In some embodiments, hydrogels have been synthesized that display heparin binding domains (HBD) that could have either the natural heparin binding affinity, or elevated affinity. These domains can sequester heparin and subsequently, bind and slowly release growth factors, providing a controlled delivery based on release rate. Growth factor delivery will also be dependent on enzymatic hydrogel degradation. As a result, hydrogels have been created that can both act as a substrate for tTG and that also contain an MMP site for degradation. The degradation rate will vary based on the number of MMP sites within the hydrogel. Additional details are described herein.

Embodiments of the present disclosure provide for hydrogels and methods of use that utilize the inherent characteristics of cancer cells—their enhanced migration and directed or controlled chemotaxis—and combine them with the release of cancer killing polypeptides or polypeptoids. Embodiments of the hydrogel are unique in that they use simultaneous, well-controlled three-dimensional patterning and/or release of multiple classes of bioactive molecules upon or from within a single biomaterial scaffold.

Hydrogel and Methods of Use

As mentioned above, embodiments of the present disclosure include hydrogels. In an embodiment, the hydrogel includes a random coil polypeptide substrate to form the hydrogel. The phrase "random coil" refers a polymer conformation where monomer units are bonded to adjacent units but prior to any crosslinking reaction, are orientated randomly in space, within an aqueous media. The random coil feature of the hydrogel is advantageous because protease or crosslinking enzymes can work more easily on flexible, random-coil proteins than on self-associated or crosslinked proteins.

Embodiments of the random coil polypeptide polymer substrate hydrogel include a glutamine-containing ("Q") block and a lysine-containing ("K") block. The Q block includes a short amino acid sequence that comprises a "Q substrate" for transglutaminase enzyme, including at least one glutamine amino acid group (also referred to as "glutamine group"). The K block includes a short amino acid sequence that comprises a "K substrate", including at least one lysine amino acid group (also referred to as "lysine group"). Either one or both of the Q block and a K block can include a random coil substrate. In addition, either one or both of the Q block and a K block can include a bioactive substrate (e.g., adhesion substrate, attraction substrate, protease substrate, killing substrate, and the like) that can be used to attract, release agents to attract, adhere to, and/or kill cancer cells. Additional details regarding the random coil substrate and the bioactive substrate are described below.

In an embodiment, the random coil polypeptide polymer substrate hydrogel can include a biocompatibility substrate or a biocompatibility substance. In an embodiment, either one or both of the Q block and a K block can include the biocompatibility substrate. In another embodiment, the biocompatibility substance is associated (e.g., disposed within the hydrogel, associated with the hydrogel, bonded to hydrogel, and the like) with the hydrogel after formation of the hydrogel. Additional details regarding the biocompatibility substrate are described below.

In an embodiment, the random coil polypeptide polymer substrate hydrogel can include a bioactive substance. The bioactive substance can include an agent or a bioactive substrate. In particular, the bioactive agent can be a cell-adherent or growth factor-adherent element (amino acid sequence or element). As noted above, the bioactive substrate can be included in an amino acid sequence element within the Q block and/or the K block. In an embodiment, the agent can include a tethered/releasable chemoattractant, chemotherapeutic, analgesic, opiate, antibiotic, or a combination thereof. In an embodiment, the bioactive substance can be associated with (e.g., disposed within the hydrogel, bonded to hydrogel, and the like) the hydrogel after formation of the hydrogel. Additional details regarding the bioactive substance are described below.

The Q substrate is designed to have a specific amino acid length, which can be used to control the characteristics (e.g., cross-linking density, material viscoelasticity, in vivo biodegradation rate, and the like) of the hydrogel. In an embodiment the Q substrate can be 3 to 12 amino acids long, or, preferably 4 to 7 amino acids long. In an embodiment, the Q substrate can include 1 to 12 or 1 to 4 glutamine groups. In an embodiment, the glutamine groups can be even spaced apart within the Q substrate. The number of glutamine groups is at least in part dependent upon the number of lysine groups, the desired characteristics (e.g., cross-linking density, etc.) of the hydrogel, and the like. In an embodiment, the Q substrate can have any of the following sequences or combinations of sequences: GQQQLGGAGTGSA (SEQ ID NO. 1), GAGQGEA (SEQ ID NO. 2), QQ, QQQ, GLQQQ (SEQ ID NO. 3), LQQQG (SEQ ID NO. 4), and GLQQQG (SEQ ID NO. 5) (JOURNAL OF THE AMERICAN CHEMICAL SOCIETY, 125 (47): 14298-14299 Nov. 26, 2003, which is incorporated herein by reference). In general, it is best if the amino acid sequence of the Q substrate is designed so that there are no, or very few, anionic (negatively charged) residues near the Q monomers (e.g., it is best to exclude glutamic and aspartic acid residues). In addition, the local polypeptide chain flexibility engendered by including simple glycine residues near the substrate Q monomers can accelerate the crosslinking reaction.

The K substrate is designed to have a specific amino acid length, which can be used to control the characteristics (e.g., cross-linking density, density of functionalization, material viscoelasticity, or in vivo biodegradation rate, and the like) of the hydrogel. In an embodiment the K substrate can be 1 to 12, or 3 to 21 amino acids long. In an embodiment, the K substrate can include lysine amino acids are 1 in 3 of the amino acids in the protein, to 1 in 85 lysine groups within the protein. In an embodiment, the lysine groups can be even spaced apart in the K substrate, or, spaced evenly within "blocks" of amino acid residues in the protein polymer. An optimal choice of the number of lysine groups is at least in part dependent upon the number of glutamine groups, the desired characteristics (e.g., cross-linking density, etc) of the hydrogel, and the like. In an embodiment, the K substrate can have any of the following sequences or combination of these sequences, for example: $(GKGTGA)_nG$ (also referred to as $(SEQ\ ID\ NO.\ 6)_nG$), $(GKGSGKGA)_nG$ (also referred to as $(SEQ\ ID\ NO.\ 7)_nG$), and $(GKAGTGSA)_nG$ (also referred to as $(SEQ\ ID\ NO.\ 8)_nG$), where n can have a lower range number of about 1, 10, 20, 30, 40, 50, 60, 70, 80, 90, 100, 110, 120, 130, 140, 150 or 160, and a higher range number of about 30, 60, 100, 120, 150, 180, 200, 300, 400, 500, or 600 (e.g., about 10 to 150, about 30 to 120, about 30, about 60, or about 120). However, even simple polylysine could be used, since the enzyme used to carry out a mild crosslinking reaction of lysine to glutamine monomers within a polypeptide or a protein, transglutaminase, generally is quite tolerant of variation in the amino acid context of the lysine residue, and indeed, will easily accept simpler primary amines such as those found in spermidine or cadaverine. (JOURNAL OF THE AMERICAN CHEMICAL SOCIETY, 125 (47): 14298-14299 Nov. 26, 2003; and: BIOCHEMISTRY, Volume: 48 Issue: 12 Pages: 2654-2660 Published: Mar. 31, 2009, each of which is incorporated herein by reference). In general, however, the higher the frequency of K monomers in the protein substrate, the higher the variability in the crosslinking product, and the higher the non-specific cytotoxicity of that protein substrate to the transglutaminase; for biomedical implantation, a low non-specific cytotoxicity is ideal.

The Q block and the K block become crosslinked to one another via one or more glutamine groups of the Q block and one or more of the lysine groups of the K block. Specifically, the "blocks" (regions of specific, repeating amino acid sequences, such as repeats of the Q substrates or the K substrates) can be enzymatically crosslinked using an enzymatic crosslinking agent. In an alternative embodiment, the blocks can be chemically, physically, and/or biologically crosslinked. In an embodiment, the crosslinking of a Q block and a K block occurs via a condensation reaction of a glutamine group and a lysine group. The degree of crosslinking depends at least in part upon the crosslinking agent (for instance, there are different transglutaminase enzymes that can be used), the number of glutamine groups and lysine groups, the particular sequence context of the substrate K and Q monomers, the overall solution concentration of the substrate materials, temperature, and the like.

The degree of crosslinking can be controlled, for instance, by varying the active units of enzyme that are utilized, in a particular ratio to the overall mass concentration of the substrate protein per unit volume of the aqueous buffer. The enzymatic cross-linking agent can be selected from tissue transglutaminase 2 and the Factor XIIIa enzyme derived from the blood dotting cascade (FASEB JOURNAL, Volume: 21, Issue: 8, Pages: 1627-1632, Published: June 2007, which is incorporated herein by reference), and the particular protein may derive from a variety of tissues, or organisms. For instance, one could use a liver-derived transglutaminase enzyme extracted from guinea pig. Alternatively, a particular transglutaminase may be expressed recombinantly in a simple organism such as E. Coli bacteria. In an embodiment, the transglutaminase can be tissue transglutaminase, transglutaminase 2, or other enzyme from among the class of transglutaminase enzymes. In a particular embodiment, the transglutaminase is a human-derived transglutaminase 2 because a material that is crosslinked with a human enzyme can safely be used in a human patient. In a particular embodiment, the transglutaminase is tissue transglutaminase because this enzyme can be expressed recombinantly in good yield and with good enzyme activity.

In an embodiment, the hydrogel was formed using a K block including one cationic K substrate that contains evenly spaced lysine substrates and a Q block including a Q substrate that contains evenly spaced glutamine substrates for tissue transglutaminase 2 (tTG). Upon the addition of the tTG enzyme, rapid crosslinking of the K substrate to the Q substrate occurs to form a self-supporting hydrogel within 2 minutes. Certain of these enzymatically crosslinked protein polymer hydrogels have been shown to have low-to-zero toxicity to normal cells and to be degradable by cellular proteases such as plasmin.

As noted above, either or both of the Q block or K block can include the random coil substrate. In an embodiment, the Q block includes the random coil substrate. The Q substrate or K substrate can be covalently bonded to the random coil substrate. Use of the random coil substrate is advantageous because the crosslinking enzyme has good access to K and Q substrate amino acids. In an embodiment, the random coil substrate protein can be composed of any number of repeating or interspersed blocks of any of the following amino acid sequences or combinations thereof: GKGSGKGA (SEQ ID NO. 7), GKGTGA (SEQ ID NO. 6), GKAGTGSA (SEQ ID NO. 8), (GQQQLGGAGTGSA)$_2$ (also referred to as (SEQ ID NO. 1)$_2$), or (GAGQGEA)$_3$ (also referred to as (SEQ ID NO. 2)$_3$).

As noted above, either or both of the Q block or K block can include additional bioactive substrates. The Q substrate or K substrate can be covalently or physically bonded to the bioactive substrates, and may either remain integral to the protein or be released over time. The bioactive substrates can be peptides or proteins that attracts (e.g., release agents that attract cancer cells), adheres to, traps, and/or kills, a certain cell type (e.g., a cancer cell).

In general, the cell type can be a pathogenic cell that causes or is capable of causing a disease such as cancer. In an embodiment, the cell type can include a cancer cell, such as cancer human cells and/or precancerous human cells. In an embodiment, the cancer cells can include cancer cells such as metastatic cancer cells. In an embodiment, the cancer human cells can include human cancer cells such as metastatic human cancer cells. The cell types can correspond to cancers such as those defined above. In particular, the cell types can include prostate cancer cells, breast cancer cells, brain cancer cells, ovarian cancer cells, bladder cancer cell, lung cancer cells, and colon cancer cells, in humans or mammals. Although cancer and cancer cells are referred to herein, the cancer and cancer cells can be replaced with pathogenic cell.

As noted above, the bioactive substrate (or the bioactive substance) can include an adhesion substrate, an attraction substrate, and a killing substrate. A single bioactive substrate can include one, two, or all three of these functions (e.g., adhesion, attraction, and/or killing). In an embodiment, the bioactive substrate include only has one of these functions. In an embodiment, the bioactive substrates can include cell-adherent or growth factor-adherent substrates.

In an embodiment, the attraction substrate functions to attract a specific cell type into the hydrogel. In other words, the attraction substrate and the cell have an affinity for one another. In an embodiment, the attraction substrate releases a substance that the cancer cells are attracted to. In an embodiment, the attraction can be short term (e.g., milliseconds to seconds) in nature or could be longer term (e.g., minutes to hours) in nature. The hydrogel can be designed to have a gradient of attraction substrates distributed in the hydrogel. In an embodiment, the quantity of attraction substrates can increase from the outside to the inside middle portion of the hydrogel so that the cells are drawn into the middle (e.g., core) of the hydrogel. In an embodiment, a single type of attraction substrate can be used to attract one type of cell. In another embodiment, a single type of attraction substrate can be used to attract two or more types of cells. The selection of the attraction substrate depends at least in part upon the desired cells to attract to the hydrogel, the other substrates in the Q block and/or K block, other components in the hydrogel, and the like.

In another embodiment, the hydrogel can include two or more types of attraction substrates, where each attraction substrate is used to attract a different type of cell. In embodiments attracting two or more types of cells, the cells being attracted can both be related to a disease (e.g., a specific cancer) but are better attracted using two different types of attraction substrates. When two or more attraction substrates are included in the hydrogel, the attraction substrates can be included in one of the Q block and the K block or a different attraction substrate is included in each of the Q block or the K block. The design of a specific hydrogel can be based on the number of attraction substrates, the interaction of the attraction substrates with one another, the interaction of the attraction substrates with the other substrates in the Q block and/or K block, and the like.

In an embodiment, the attraction substrate can be any of the following: Insulin-like Growth Factor (IGF-1), osteopontin, osteonectin, Epidermal Growth Factor 1 (EGF-1), Stromal Derived Factor 1 (SDF-1), bone morphogenetic protein factors such as BMP-1, and/or BMP-2, or Colony Stimulating Factor 1, (CSF-1), each of which has a sequence(s) that is known in the art.

As noted above, the hydrogel can include one or more types of adhesion substrates (or adhesion substances). The adhesion substrate interacts with and adheres to (e.g., traps) the cell for a period of time. The time frame for will depend upon the adhesion substrate and its strength in adhering to the cell, the cell type, the other components of the hydrogel, the purpose of the hydrogel, and the like. The time frame can be from minutes to hours to days.

In some instances the adhesion substrate and the attraction substrate can be the same depending upon the length of time the adhesion substrate interacts with the cell. In an embodiment, the attraction substrate is a cell-adherent or growth factor-adherent substrate. In an embodiment, inclusion of both the attraction substrate and the adhesion substrate indicates that the two substrates are not the same. In this instance, the attraction substrate causes the cells to enter the hydrogel and the adhesion substrate causes the cells to be trapped in the hydrogel for a period of time.

In an embodiment, the hydrogel can be designed so that the adhesion substrate or adhesion substance is disposed in a certain portion of the hydrogel (e.g., the core) so that the cancer cells are not exposed to the subject or so the cancer cells are disposed close to the killing substrates or killing substances.

In an embodiment, a single type of adhesion substrate can be used to adhere to one type of cell. In another embodiment, a single type of adhesion substrate can be used to adhere to two or more types of cells. The selection of the adhesion substrate depends at least in part upon the desired cells to adhere to the hydrogel, the other substrates in the Q block and/or K block, other components in the hydrogel, and the like.

In another embodiment, the hydrogel can include two or more types of adhesion substrates, to improve the adherences of target cancer cells. When two or more adhesion substrates are included in the hydrogel, the adhesion substrates can be included in one of the Q block and the K block or a different adhesion substrate is included in each of the Q block or the K block. The design of a specific hydrogel can be based on the number of adhesion substrates, the interaction of the adhesion substrates with one another, the interaction of the adhesion substrates with the other substrates in the Q block and/or K block, and the like.

In an embodiment, the adhesion substrate can be any of the following: a peptide containing the RGD amino acid sequence (RGD peptide), PHSRN (SEQ ID NO. 14) and KQAGDV (SEQ ID NO. 15) from fibronectin, and YIGSR (SEQ ID NO. 16) from elastin, cadherin proteins such as N-cadherin. As noted above, the hydrogel can include one or more killing substrates (or killing substances). These killing substrates can be tethered to the hydrogel, or directly mixed into the hydrogel, or pre-formulated into polymeric microparticles/nansparticles and then mixed into hydrogel. The killing substrate is used to kill or otherwise destroy a cell type or harm the cell so that the cell can not cause the disease or function to cause the disease. In an embodiment, the cell type is a cancer human cell type such as a cancer cell. In an embodiment, the killing substrate is selected to kill a specific cell type while not harming other non-cancer cell types. In an embodiment, the killing substrate is selected to kill a specific cell type but may cause harm to other cell types. In this regard, the hydrogel can be designed so that the killing substrate is embedded within the hydrogel so that that killing substrate has limited interaction with non-cancer cells.

In an embodiment, the killing substrate is disposed within the hydrogel and delivered locally to limit exposure to non-cancer cells. In addition to the killing substrate, the hydrogel includes an attraction substrate and/or adhesion substrates. In this regard, the attraction substrate causes the cancer cells to enter the hydrogel/or remain locally, which will increase the drug availability to target cancer cells and achieve high treating efficacy.

In an embodiment, a single type of killing substrate can be used to kill one type of cell. In another embodiment, a single type of killing substrate can be used to kill two or more types of cells. The selection of the killing substrate depends at least in part upon the drug efficiency and selectivity, the desired cells to kill, the other substrates in the Q block and/or K block, other components in the hydrogel, and the like.

In another embodiment, the hydrogel can include two or more types of killing substrates, where each killing substrate is used to kill a different type of cell. In embodiments where it is desired to kill two or more types of cells, the cells being killed can both be related to the disease (e.g., a specific cancer) but are better killed using two different types of killing substrates. When two or more killing substrates are included in the hydrogel, they can be separately tethered to the hydrogel, or directly mixed into the hydrogel, or pre-formulated into polymeric microparticles/nanoparticles and then mixed into hydrogel. The design of a specific hydrogel can be based on the number of killing substrates, the interaction of the killing substrates with one another, the interaction of the killing substrates with the other substrates in the Q block and/or K block, and the like.

In an embodiment, the killing substrate can have any of the following: conventional chemotherapeutics for target cancer types, agents that can assist killing of other therapies, novel chemotherapeutics such as a polypeptide or peptidomimetic compound such as a sequence-specific peptoid.

As noted above, the hydrogel can further include a biocompatibility substrate (or substance). The biocompatibility substrate functions to allow the hydrogel to interact with the subject without causing an immune response specific to the introduction of the hydrogel to the subject. In particular, the biocompatibility substrate reduces or eliminates the adverse (e.g., toxic, specific immune response, and the like) local and/or systemic effects. In addition, the biocompatibility substrate reduces or eliminates induced undesirable effects. In particular, the use of biocompatibility substrates may aid in preventing a localized immune response and discourage non-specific, non-cancerous cell invasion. In an embodiment, a hydrogel including a biocompatibility substrate does not cause a non-specific immune response as a result of being disposed into the subject.

In an embodiment, a single type of biocompatibility substrate can be used. The selection of the biocompatibility substrate depends at least in part upon the substrates in the Q block and/or K block, other components in the hydrogel, and the like.

In another embodiment, the hydrogel can include two or more types of biocompatibility substrates, where each biocompatibility substrate serves a different biocompatibility function. When two or more biocompatibility substrates are included in the hydrogel, the biocompatibility substrates can be included in one of the Q block and the K block or a different biocompatibility substrate is included in each of the Q block or the K block. The design of a specific hydrogel can be based on the number of biocompatibility substrates, the interaction of the biocompatibility substrates with one another, the interaction of the biocompatibility substrates with the other substrates in the Q block and/or K block, and the like.

In an embodiment, the biocompatibility substrate (and can be referred to as a biocompatibility substance) can be attached or graphed to one or both of the Q block and K block prior to, during, and/or after the formation of the hydrogel. In these embodiments, the biocompatibility substrate is not part of the backbone of the random coil protein polymer.

In an embodiment, the biocompatibility substrate or substance can be synthetic polymers, such as, n-MEG, a poly (ethylene glycol) (PEG), poly(vinyl alcohol) (PVA), poly (acrylic acid) (PAA), poly(propylene furmarate-co-ethylenee glycol) (P(PF-co-EG)), polyacrylamide, polypeptides, poly-N-substituted glycine oligomers (polypeptoids), and the like, while naturally derived polymers normally include hyaluronic acid (HA), alginate, chitosan, agarose, collagen, fibrin, gelatin, dextran, and any combination thereof, as well as derivatives of each of these.

In an embodiment, the PEG can be a linear PEG, a multi-arm PEG, a branched PEG, and combinations thereof. The molecular weight of the PEG can be about 1 kDa to 100 kDa, about 1 kDa to 50 kDa, about 1 kDa to 40 kDa, about 1 kDa to 30 kDa, about 1 kDa to 20 kDa, about 1 kDa to 12 kDa, about 1 kDa to 10 kDa, and about 1 kDa to 8 kDa. When used in reference to PEG moieties, the word "about" indicates an approximate average molecular weight and reflects the fact that there will normally be a certain molecular weight distribution in a given polymer preparation.

In an embodiment, a hydrogel including PEGs (also referred to as a hybrid hydrogel) has been fromed, where (1) K block (with its available lysines) is pegylated with N-succinimidyl-PEG (avg. molar mass less than 10,000 g/mol, so still safe to be passed through kidneys on its own); then (2) Q block is mixed in with K block, plus (3) a multi-arm PEG crosslinker is added. The PEGylation of the K protein compatibilizes the proteins with the PEGs, so that an IPN (interpenetrating network) of protein and PEG are formed. The PEG in this hybrid hydrogel can play one or more roles: (1) it slows down the enzymatic degradation of the hydrogel, for longer times as the fraction of PEG gets higher; (2) it reduces the inflammatory and immune response of the body to the hydrogel implant.

In an embodiment, the biocompatibility substrate can include star polymers. Star polymer can be synthesized by ring-opening polymerization to create a material with uniform, structurally controllable, globular, quad-functional (core, periphery, polymer, interstitial regions) nanoparticle structures. Biodegradable polycaprolactone (PCL) forms the star's core, surrounded by a hydrophilic shell formed by PEG arms. While multi-armed PEG is available commercially, the synthetic strategy we use to make our star PEGs allows the inclusion of a biodegradable PCL core and does not require heavy metal catalysis during synthesis. The number of arms and arm length, reactive end-groups, and molecular weight can be controlled and tailored for the specific hydrogel. In an embodiment, star polymers having a size of about 20-100 nm in diameter, with about 4 to 30 arms displaying terminal chemical functionality. The functional domains allow for covalently attaching reactive groups for chemical or enzymatic crosslinking into a hydrogel. By controlling the composition and number of PEG arms, the partitioning between the core-forming and arm-forming polymers can be varied to control hydrogel properties, ultimately affecting cancer cell behavior.

QQ, QQQ, GLQQQ (SEQ ID NO. 3), LQQQG (SEQ ID NO. 4), and GLQQQG (SEQ ID NO. 5), with various repeating lengths, and including one or more of the appropriate blocks noted in Table 1 (e.g., RDG block). In an embodiment, the K block can have the sequences as shown in Table 1. In an embodiment, it is envisioned that the K block could have any sequences with multiple K distributed throughout the sequences, which can give rise to water soluble protein polymers that do not form complicated secondary structures as well as including one or more of the appropriate blocks noted in Table 1 (e.g., RDG block). As noted above, the design of the hydrogel can be based on the design of each of the Q block and the K block. In most instances, the hydrogel is designed considering the design of both the Q block and the K block so that the hydrogel has the appropriate functions and characteristics of the desired hydrogel.

As mentioned above, the random coil polypeptide polymer substrate hydrogel can include a bioactive substance that is an agent. In an embodiment, the agent can include chemoattractants, chemotherapeutics (also referred to as killing substances), or a combination therefore. In an embodiment, the agents can be released into the hydrogel and in the case of chemoattractants, can be released into the area around the hydrogel. In an embodiment, the agent can be associated with (e.g., physically disposed within the hydrogel, attached to hydrogel, and the like) the hydrogel after formation of the hydrogel. The agent is included to impart a characteristic to the hydrogel such attracting certain types of cells to the hydrogel (e.g., chemoattractant) or giving the hydrogel the ability to kill the cells or certain types of cells (e.g., chemotherapeutic) that enter the hydrogel or enter a portion of the

TABLE 1

Summary of block compositions in the protein polymer

| Name | Block composition | Function |
|---|---|---|
| K4 (SEQ ID NO. 7)n | $(GKGSGKGA)_n$, n = 1 to 300 (e.g., 30, 60, 120) | Lysine (K) sub-strate for TG2 |
| K6 (SEQ ID NO. 6)n | $(GKGTGA)_n$, n = 1 to 300 (e.g., 30, 60, 120) | Lysine (K) sub-strate for TG2 |
| K8 (SEQ ID NO. 8)n | $(GKAGTGSA)_n$, n = 1 to 300 (e.g., 30, 60, 120) | Lysine (K) sub-strate for TG2 |
| BQ (SEQ ID NO. 1)n | $(GQ3LG2AGTGSA)_n$, n = 1 to 300 (e.g., 30, 60, 120) | Glutamine (Q) substrate for TG25 |
| PZ (SEQ ID NO. 2)3 | $(GAGQGEA)_3$ | Domain to increase protein water solubility |
| MMP SEQ ID NO. 9 | GPQGIWGQ | Substrate for MMP 2 |
| RGD SEQ ID NO. 10 | ITVYAVTGRGDSPASSRPI | Cell adhesion signal[2] |
| RDG SEQ ID NO. 11 | ITVYAVTGRDGSPASSRPI | Scrambled cell adhesion signal |
| HBD A SEQ ID NO. 12 | $G(R_4A)_3G$ | Heparin binding domain: higher affinity |
| HBD B SEQ ID NO. 13 | $GRP(RA)_4RDQTRG$ | Heparin binding domain: lower affinity |

In an embodiment, the Q block can have the sequences as shown in Table 1. In an embodiment, it is envisioned that the Q block could have the following sequences: GQQQLG-GAGTGSA (SEQ ID NO. 1), GAGQGEA (SEQ ID NO. 2), hydrogel. The agents can be included in hydrogels that include or do not include bioactive substances that are included in the Q block and/or the K block. In an embodiment, the hydrogel can include the agents prior to disposing in the subject. In another embodiment, the hydrogel does not include the agents when the hydrogel is disposed in the subject, but rather the agent is disposed in the hydrogel after (e.g., within minutes or days or weeks) the hydrogel is disposed in the subject.

In an embodiment the agent can be placed strategically within the hydrogel to enhance the hydrogel. For example, the chemoattractants can be disposed on the outside portions of the hydrogel to induce the cancer cells to migrate into the hydrogel. In another embodiment, the chemoattractants can be disposed as a gradient to induce the cancer cells to enter deep into the hydrogel. In an embodiment, the chemotherapeutic can be disposed deep within the hydrogel so that the harm they can cause non-cancer cells is reduced. A combination of a gradient of the chemoattractants and chemothera- Thus, embodiments of the present disclosure can achieve such goals using attraction substrates and/or chemoattractants.

Some exemplar chemotherapeutics include methotrexate, 5-fluorouracil, doxorubicin, docetaxel, as well as other drugs for chemotherapy, radiotherapy, photodynamic therapy. Additional chemotherapeutics are described herein.

Different chemoattractants can be chosen with regard to the cancer types of interest. As an example, Table 2 summarizes chemoattractant candidates for breast cancer. The efficacies and dosages of chemoattractants are being characterized by in vitro chemotaxis assays. The chemotactic effects of an important candidate, stromal cell-derived factor 1 (SDF-1), have been confirmed in vitro using the transwell assay.

TABLE 2

| | Factors for breast cancer- to be tested by in vitro chemotaxis assays |
|---|---|
| Fetal serum | Starting material which contains a broad spectrum of invasion factors. In rat and mouse mammary tumors, cells are attracted to blood vessels where they intravasate. |
| SDF-1 | The chemokine SDF-1 induces chemotaxis and invasion in breast cancer cells. |
| EGF | EGF receptor expression is correlated with poor prognosis in breast cancer. EGF and TGFa are chemotactic for breast carcinoma cells in vivo. |
| TGF-α | See above |
| CSF-1 | CSF-1 and CSF-1-receptor expression is correlated with invasive mammary tumors in both human populations and animal models. CSF-1 is chemotactic for macrophages in vivo. |
| VEGF-a | VEGF-α is correlated with angiogenic response and has been shown to stimulate invasion in breast cancer cells. |
| FGF-1 | FGF-1 expression is correlated with malignancy of breast tumors. |
| PDGF B/B | PDGF B/B is produced by macrophages and stimulates cell motility in connective tissue cells, monocytes and neutrophils, and is correlated with invasion in a number of human cancers. Furthermore, PDGF receptor beta, which responds to PDGF B/B is found on monocytes and macrophages. |
| HGF | HGF stimulates tumor cell-cell interactions, matrix adhesion, migration, invasion, and angiogenesis. |
| Lpa | LPA stimulates cell proliferation, migration and survival by acting on its cognate G-protein-coupled receptors. |
| Heregulin | Heregulin has been shown to enhance motility and migration of cancer cells and as the ligand for the ErbB2/ErbB3 heterodimer has been shown to enhance cell proliferation in breast cancers. |
| ETs1-3 | Endothelins 1-3 and their receptors are reported to mediate chemotaxis in a variety of cell types including carcinoma cells. It is proposed that ETs are involved in invasion of breast tumors. |
| CCLx | The CC chemokines CCL2, CCL3, CCL4, CCL5, and CCL8 are involved in leukocyte recruitment in mammary tumors. | peutic can be used to induce the cancer cells deep into the hydrogel where the chemotherapeutics are located in the hydrogel to maximize the killing of the cancer cells.

Embodiments of the chemoattractants and chemotherapeutics can be associated with the hydrogel or the chemoattractants and chemotherapeutics can be disposed in a capsule (e.g., microparticles, nanoparticles, etc.) which is then associated with the hydrogel.

The types and amounts of agent used will depend at least in part upon the agent, the components of the Q block and the K block (e.g., inclusion or exclusion of certain bioactive substrates), the disease, and the like. Illustrative chemoattractants and chemotherapeutics are described below, but embodiments of the present disclosure are not limited to those described below and it is envisioned that other types of chemoattractants and chemotherapeutics can be used in embodiments of the present disclosure.

In order for the cancer cells to migrate to the hydrogel, the hydrogel needs to display and/or release of appropriate signals in the system to attract the infiltration of cancer cells and hence to minimize their tendency to depart from the surgical site and invade other tissues. Selective migration of cancer cells within a mixed cell population can be achieved based on a difference in the chemotactic response of normal cells and cancer cells. Receptor expression studies have shown a marked difference in the "preferred" stimuli as well as the magnitude of the ligand binding response in cancer cells.

For the in vivo delivery of these chemoattractants, chemoattractant-loaded microspheres can be sued which will be further trapped (e.g., physically, chemically, and/or biochemically) in the hydrogel scaffolds, to protect encapsulated factors and achieve a long-lasting release. In an embodiment, gelatin microspheres and poly(lactic-co-glycolic acid) (PLGA) microspheres can be used and selected based on their protecting effects and releasing files.

In an embodiment, the chemotherapeutics should be effective in killing surrounding cancer cells while being relatively safe to normal tissues. Conventional chemotherapeutics can be used in the hydrogel, chosen with regard to the cancer types. In addition, other candidate chemotherapeutics that could be used include cationic, amphipathic peptidomimetics, with an aim towards biostable compounds that are effective and selective towards cancer cells, unaffected by common mechanisms of chemoresistance, and are easy to be further modified (for example, tethered to the hydrogel).

Some recent studies have highlighted potential applications of some natural and synthetic cationic, amphipathic peptides (CAPs) as a new class of anti-cancer drugs, and it is contemplated that these could be used in embodiments of the present disclosure. CAPs generally adopt a structure in which clusters of cationic and hydrophobic residues are spatially organized in discrete sectors. Electrostatic interactions through their cationic residues select for anionic membranes; hydrophobic regions are then responsible for their membrane permeation and disruption. Their selectivity towards cancer cells could be due to the changed properties of cancer cell membranes in contrast to normal tissue cell membranes, with regard to membrane charges, fluidity, transmembrane potential, etc.

However, CAPs are limited in their clinical usage due to their susceptibility to rapid in vivo proteolysis. Poly-N-substituted glycines (peptoids), in which side chains are attached to the backbone nitrogen rather than the α-carbon, are excellent candidates to mimic CAPs. They are resistant to protease degradation, and can be easily synthesized with diverse sequences at relatively low cost, not being limited to natural amino acids. Moreover, previous findings have indicated that peptoids can be designed to form stable helical secondary structures via the periodic incorporation of bulky, α-chiral side chains, resulting in a helical repeat of about 3 monomers per turn and a helical pitch of 6.0-6.7 Å, which makes it easy to display discrete cationic and hydrophobic faces along peptoid helical axis.

A library of cationic, amphipathic peptoid oligomers ("capetoids") with various chain lengths, charges, helicity, hydrophobicity and amphipathicity have been synthesized. Their activities towards several in vitro cultured cancer cell lines were tested via MTS assays. Primary dermal fibroblasts and freshly isolated red blood cells were also tested to estimate their biosafety. Several peptoids were found to display higher activities towards these cancer cell lines than primary dermal fibroblasts, showing limited hemolytic effects, as summarized in Table 3. In some concentration ranges, these peptoids kill cancer cells efficiently while being relatively safe to primary dermal fibroblasts. Doxorubicin and docetaxel which are clinically used chemotherapeutics killed primary fibroblasts as efficiently as cancer cell lines in vitro (Data not shown). Furthermore, the actions of these peptoids were not affected by the known multidrug resistance. In MCF 7 cells and the multidrug resistant MCF 7 cells (kindly provided by Prof. Brandy Sikic at Stanford) which overexpress P-glycoproteins, these peptoids had similar cytotoxicities. The multidrug resistant MCF7 cells did not display resistance to these peptoids.

To summarize, some capetoids have been developed that showed promising anti-cancer activities and can overcome the known multidrug resistance and these could be used in embodiments of the hydrogel.

It was shown by Moreau et al. (See: E. Moreau, K. Anderson, J. R. Mauney, T. Nguyen, D. L. Kaplan, M. Rosenblatt, "Tissue-Engineered Bone Serves as a Target for Metastasis of Human Breast Cancer in a Mouse Model", *Cancer Research* 2007; 67: (21). Published Nov. 1, 2007, 10304-10308), which is incorporated herein by reference) that cancer cells from a human-derived prostate cancer cell line, if transplanted into a mouse model of human cancer (an "orthotopic" model), will migrate from a mouse's circulating blood stream and effectively "metastasize" (become lodged, and then proliferate and form a new tumor) within two different, implanted sources of bone morphogenic factor 2 (BMP-2), either: (1) a piece of fresh human bone, or (2) a silk protein-based implant aggregated via hydrogen bonding into a biomaterial aggregate characterized by a high content of beta-sheet structure and very low water content. Fresh, living human bone naturally releases BMP-2, while the silk scaffold was impregnated with the BMP-2 protein and released BMP-2 as it slowly degraded in vivo. This result shows that growth factors such as BMP-2 can serve as powerful chemoattractants for certain cancer cells. Even cancer cells that are, initially, freely circulating in the bloodstream, can be attracted and will settle and proliferate within either a biological or biosynthetic implant that releases BMP-2. Logically, then, if an implant that releases a growth factor/chemokine such as BMP-2 is placed within the tissue very near to the position in the body where metastatic cancer cells are likely to be found (specifically, at a surgical site from which cancerous tumor tissue has been removed), any migratory cancer cells in the tissue that immediately surrounds would be likely to migrate and effectively "metastasize" into this implant, to the extent that the material is hydrated, porous, cell-permeable, and provides cell-adherent moieties that allow cancer cell migration onto and within the implant. The placement of such an implant within the tissue for the purpose of collecting local, as opposed to freely circulating, cancer cells are taught by embodiments of the present disclosure.

As described in some detail above, the hydrogel is a reaction product that includes a biocompatibility substrate. The reaction product is formed from a Q block and a K block in the presence of an enzymatic cross-linking agent. As described above, the Q block includes a Q substrate including at least one glutamine group and the K block includes a K substrate including at least one lysine group. Upon reaction with the enzymatic cross-linking agent the Q block and the K block are cross-linked to one another via one or more glutamine groups of the Q block and one or more of the lysine groups of the K block to form a random coil polypeptide polymer substrate.

TABLE 3

Peptoid toxicities. $LC_{10/50}$ means lethal concentrations causing 10% or 50% of cancer cell death. Cell viability was evaluated via MTS assay in cells treated with compounds for 24 h. $HC_{10}$, concentration causing 10% hemolysis of human RBCs.

| compounds | Peptoid sequences | $LC_{50}$ (mM) | | | | | $HC_{10}$ (mM) |
| --- | --- | --- | --- | --- | --- | --- | --- |
| | | MEL28 (Melanoma) | Lncap (prostate cancer) | MCF7 (breast cancer) | Ovcar3 (ovarian cancer) | Primary dermal fibroblast | Red blood cells |
| Peptoid 1 | H-(NLys-Nspe-Nspe)$_4$-NH$_2$ | 5.0 | 5.0 | 4.5 | 6.5 | 5.0 | 21 |
| 1$_{11mer}$ | H-(NLys-Nspe-Nspe)$_3$-NLys-Nspe-NH$_2$ | 15.0 | 8.0 | 9 | 10.5 | 18.5 | 103 |
| 1$_{achiral}$ | H-(NLys-Npm-Npm)$_4$-NH$_2$ | 18.5 | 10.5 | 15 | 16 | 39.5 | 183 |
| 1-Npm$_{2,3,8,9}$ | H-(NLys-Npm-Npm-NLys-Nspe-Nspe)$_2$-NH$_2$ | 16.5 | 10.5 | 10 | 11 | 18.5 | 80 |
| 1$_{achiral}$-Nspe 2 | H-NLys-Nspe-Npm-(NLys-Npm-Npm)$_3$-NH$_2$ | 18.0 | 8.5 | 14.5 | 15.5 | 36.5 | 160 |

As described above, the one or both of the Q block and the K block include a random coil substrate. In addition, one or both of the Q block and the K block can include one or more bioactive substrates. Furthermore, one or both of the Q block and the K block can include one or more biocompatibility substrates. As mentioned above, one or more biocompatibility substrates can be added to the hydrogel after the hydrogel is formed and/or the biocompatibility substrate can be added after the formation of the Q block and/or the K block. Once the hydrogel is formed, bioactive substances can be added to the hydrogel. As noted above, the bioactive substances can be associated with the hydrogel.

Embodiments of the present disclosure also include a method of making a hydrogel. The method includes reacting a Q block and a K block in the presence of an enzymatic cross-linking agent. The enzymatic cross-linking agent causes the glutamine group of the Q substrate and the lysine group of the K substrate to crosslink. As described above, the one or both of the Q block and the K block include a random coil substrate. In addition, one or both of the Q block and the K block can include one or more bioactive substrates. Furthermore, one or both of the Q block and the K block can include one or more biocompatibility substrates. As mentioned above, one or more biocompatibility substrates can be added to the hydrogel after the hydrogel is formed and/or the biocompatibility substrate can be added after the formation of the Q block and/or the K block. Once the hydrogel is formed, bioactive substances can be added to the hydrogel. As noted above, the bioactive substances can be associated with the hydrogel.

Embodiments of the present disclosure also include a method of making a hydrogel. The method includes mixing a Q block and a K block in the presence of an enzymatic cross-linking agent. The Q block includes a Q substrate including at least one glutamine group and the K block includes a K substrate including at least one lysine group. One or both of the Q block and the K block include a random coil substrate. The Q block and the K block are enzymatically cross-linked to form a random coil polypeptide polymer. Specifically, the Q block and the K block are cross-linked to one another via one or more glutamine groups of the Q block and one or more of the lysine groups of the K block. Once the cross-linking is complete, the hydrogel is formed from the random coil polypeptide polymer substrate.

The following method is an illustrative method for forming a hydrogel of the present disclosure. The amounts, pH, and the like can be modified depending upon the components used to form the hydrogel as well as the desired characteristics of the hydrogel. Thus, the following method is for illustrative purposes only and modifications to the method of making the hydrogel are envisioned to be included in the present disclosure.

In general, hydrogels can be formed through enzymatic crosslinking of K block and the Q block, such as those described herein (e.g., one or both can include a bioactive substrate or substance (e.g., adhesion substrate, protease substrate, killing substrate, and the like), biocompatibility substrate or substance, and/or the like). The K block and the Q block can be recombinant proteins created by genetic engineering, and expressed in a cultured organism such as $E.\ Coli$, and purified. In addition, the K block and the Q block proteins can undergo additional purification to remove endotoxins. For example, Triton X-114 (Sigma) can be added at 1% to protein (K block and/or Q block) dissolved at a mass concentration of up to about 10 mg/mL in endotoxin-free water and the pH can be adjusted to about 9.5. The solution can be stirred for about 30 minutes at about 4° C., placed in an about 37° C. water bath for about 10 minutes and then centrifuged at about 10,000 g at about 37° C. for about 10 minutes. The supernatant containing the protein can then be placed into a new conical tube and the process may be repeated multiple times, with pH readjustment to about 9.5 after every four rounds. After the last round of phase separation, the solution can be placed on degassed Bio-beads SM2 Adsorbents (Bio-rad Laboratories, Hercules, Calif.) to remove any remaining Triton X-114. Samples can then be dialyzed against endotoxin-free water and lyophilized. The endotoxin levels were tested using a QCL-1000 Endpoint Chromogenic LAL assay (Lonza, Walkersville, Md.). The precursor proteins for hydrogel implant formation should only be used if the endotoxins (EU) per mL of protein when dissolved at concentrations used in the hydrogels are less than 20 EU/mL.

Tissue transglutaminase (tTG) from guinea pig liver (Sigma-Aldrich Inc., Milwaukee, Wis.), for example, can be dissolved at about 0.04 units/μL in an aqueous buffer comprising, in addition to typical buffer salts, about 2 mM ethylenediaminetetraacetic acid (EDTA) and about 20 mM Dithiothreitol (DTT), at about pH 7.7. The lysine-containing ("K") protein can be dissolved at a concentration of up to about 10% (w/v) in a buffer containing about 200 mM 4-Morpholinepropanesulfonic acid (MOPS), about 20 mM $CaCl_2$, and about pH 7.6. The glutamine-containing ("Q") protein can be re-suspended at a concentration of up to about 15% (w/v) in an aqueous buffer comprising about 2 mM EDTA and about pH 7.3. In one embodiment of such an enzymatically crosslinked protein system the three components were combined at a ratio of about 1:1.5:1.5 for tTG:K block:Q block solutions. The ratio can be varied depending on the K block, Q block, desired gelation time, and desired final physical characteristics of the hydrogel, and the like. Protein precursors with enzyme were incubated at about 37° C. until gelation occurred.

In a preferred embodiment, some fraction of the particular Q proteins and K proteins used will be block co-polymers that comprise, directly within their protein sequence, bioactive polypeptide sequences such as cell adhesion sequences, protease degradation sites, or heparin binding can be incorporated into the gel as it forms by the transglutaminase crosslinking reaction. Alternatively, once the hydrogel is formed or during the formation of the hydrogel, one or more bioactive substances, one or more biocompatibility substances, and/or one or more agents (e.g., chemoattractants, chemotherapeutics, and the like) can be attached or disposed within the hydrogel.

It should also be noted that in another embodiment, the hydrogel can be formed by physical self-assembly (e.g., like silk-based or elastin-based biomaterials) and/or by chemical crosslinking (e.g., the use of a multivalent N-acryoyl succinimidyl crosslinkers). Embodiments of the hydrogel formed in this manner can include all of the substrates, agents, substances, and the like described above, where the only difference is the procedure for making the hydrogel. Embodiments of the hydrogel formed from one of these methods will have all of the characteristics of the hydrogels described above.

Embodiments of the present disclosure include methods of isolating a cancer human cell. The method includes disposing the hydrogel in a subject. The hydrogel can be disposed in the subject during a surgical procedure. For example, the hydrogel can be disposed in the subject during a surgical procedure to remove a tumor or a cancer. In another embodiment, the hydrogel can be disposed into the subject using a syringe to inject the hydrogel into a certain area of the subject. After an appropriate amount of time, the hydrogel can be removed from the subject. In an embodiment, after a certain amount of time the hydrogel can degrade within the subject.

In an embodiment, the hydrogel can include a bioactive substance or bioactive substrate (e.g., attraction substrate or substance) to attract the cancer cells. The cancer cells migrate towards and into the hydrogel.

In an embodiment, the hydrogel can include a bioactive substance or bioactive substrate (e.g., adhesion substrate or substance) to adhere to the cancer cells. The cancer cells that migrate into the hydrogel can be trapped in the hydrogel for a period of time as a result of interacting with the adhesion substrate or substance. In an embodiment, the hydrogel can include an attraction substrate or substance to attract the cancer cells into the hydrogel and then trap the cancer cells in the hydrogel using the adhesion substrate or substance.

In an embodiment, the hydrogel can include a bioactive substance or bioactive substrate (e.g., killing substrate or substance) to kill the cancer cells. The cancer cells that migrate into the hydrogel can be killed by the killing substrate or substance. In an embodiment, the hydrogel can include an attraction substrate or substance to attract the cancer cells into the hydrogel and/or trap the cancer cells in the hydrogel using the adhesion substrate or substance. Then the cancer cells can be used to kill the cancer cells.

EXAMPLES

Now having described the embodiments of the present disclosure, in general, the examples describe some additional embodiments of the present disclosure. While embodiments of present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

As described herein, we are developing hydrogels based on recombinant protein polymers as one potential scaffold. In this system, recombinant protein polymers that are engineered to present various bioactive modules can be enzymatically crosslinked into hydrogels by transglutaminase 2 (TG2). Moreover, these protein polymers can be used to make hybrid hydrogels in combination with synthetic polymers, such as poly(ethylene glycol) (PEG).

We've developed a novel protein polymer hydrogel that is enzymatically crosslinked by TG2. First, amino acid sequences were designed to produce protein polymers that are highly water-soluble, random coil, and substrates of the crosslinking enzyme, TG2; after that, the defined sequences were synthesized by controlled cloning methods. The proteins were then expressed in E. coli and purified by $Ni^{2+}$-affinity chromatography, and then further purified by prep-HPLC to remove endotoxin and other impurities. Human TG2 was expressed, purified, and used to crosslink the protein polymers. Rheological characterization of gelation was performed on protein polymers under various conditions (e.g., protein polymer concentration, chain length, crosslinking site spacing, enzyme concentration, etc.). The elasticity of the hydrogel was found to increase as the protein polymer concentration, protein polymer length, and crosslinking site density increase.

By including various bioactive sequences into the protein polymer backbone as functional blocks (Table 4), desired biological functionalities can be built into the protein polymer hydrogel system. For example, a cell adhesion signal based on the RGD sequence from human fibronectin was incorporated. To support cell infiltration into hydrogel scaffolds, peptide sequences that are sensitive to the action of matrix metalloprotease 2 (MMP 2) were also incorporated into protein polymers to allow cell-mediated degradations of scaffolds. Additionally, sequences that can bind to heparin with varying affinities have been introduced into the protein polymers.

TABLE 4

Summary of block compositions in the protein polymer

| Name | Block composition | Function |
|---|---|---|
| K4 (SEQ ID NO. 7)$_n$ | GKGSGKGA | Lysine substrate for TG2 |
| K6 (SEQ ID NO. 6)$_n$ | GKGTGA | Lysine substrate for TG2 |
| K8 (SEQ ID NO. 8)$_n$ | GKAGTGSA | Lysine substrate for TG2 |
| BQ (SEQ ID NO. 1)$_2$ | (GQ3LG2AGTGSA)$_2$ | Glutamine substrate for TG25 |
| PZ (SEQ ID NO. 2)$_3$ | (GAGQGEA)$_3$ | Domain to increase protein water solubility |
| MMP SEQ ID NO. 9 | GPQGIWGQ | Substrate for MMP 2 |
| RGD SEQ ID NO. 10 | ITVYAVTGRGDSPASSRPI | Cell adhesion signal[2] |
| RDG SEQ ID NO. 11 | ITVYAVTGRDGSPASSRPI | Scrambled cell adhesion signal |
| HBD A SEQ ID NO. 12 | G(R$_4$A)$_3$G | Heparin binding domain: higher affinity |
| HBD B SEQ ID NO. 13 | GRP(RA)$_4$RDQTRG | Heparin binding domain: lower affinity |

Biocompatibility of the hydrogels has first been characterized in vitro. First, NIH 3T3 fibroblasts were cultured on top of protein hydrogels, and cell adhesion and spreading were investigated. Hydrogels formed with RGD modified protein polymers were found to have the fastest cell adhesion, compared with the unmodified or RDG modified protein hydrogel. Cells fully spread on all protein hydrogel surfaces at 20 hour. Then, stem cell viability and proliferation were studied in vitro. Mouse mesenchymal stem cells that were luciferase positive were encapsulated in three different materials, the unmodified protein hydrogel, the protein hydrogel modified with RGD, and growth factor depleted matrigel. Bioluminescence signal was monitored over time as a measurement of the cell numbers, which indicated cell viability and proliferation. Long-term cell viability was observed in both protein hydrogels (~40% viable cells over 10 days), which were comparable with those in matrigel.

Hydrogels are being optimized via in vitro invasion assays to support cell migration/invasion. One such assay is a modified Boyden chamber invasion assay. Standard transwells with porous filter membranes on the bottom (Corning Costar) are coated with proposed hydrogels in proper thickness. With cells seeded on top of the hydrogel and chemoattractants added in the lower chamber, cell invasion through the hydrogels can be detected by staining the porous filter membrane beneath the hydrogel after certain time of cell culture. As an example (FIG. 1), a transwell was coated with a ~3 mm thick 5% (wt) protein hydrogel, the only bioactive motif in which was the MMP block. Though standard integrin binding sites (RGD motifs) was not present in the tested hydrogel, efficient spreading of MRC 5 (ATCC CCL-171, normal human embryonic lung fibroblast) cells on the hydrogel was observed at 12 h after cell seeding. With 10% FBS media placed in the lower chamber and replaced every day, MRC 5 cells migrated through the hydrogel in about 5 days, while PC3 cells, human prostate cancer cells, which are less motile than fibroblasts in vitro, did not spread very well after seeding and failed to migrate through, indicated by no cell staining on the filter membranes 5 days later. Such in vitro invasion assays will be used to optimize hydrogel properties to support the invasion of chosen cancer cell lines as well as evaluating the effects of chosen chemoattractants, as discussed later.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim the following:

1. A random coil polypeptide polymer substrate hydrogel, comprising:
   a random coil polypeptide polymer substrate including:
      a Q block including a Q substrate including at least one glutamine group;
      a K block including a K substrate including at least one lysine group; and
      a biocompatibility substrate or a biocompatibility substance,
   wherein the Q block and the K block are crosslinked to one another via one or more glutamine groups of the Q block and one or more of the lysine groups of the K block;
   wherein one or both of the Q block and the K block include a random coil protein substrate, wherein one or both of the Q block and the K block include a bioactive substrate, wherein a cancerous human cell has an affinity for the bioactive substrate.

2. The hydrogel of claim 1, wherein the bioactive substrate is selected from the group consisting of an adhesion substrate, an attraction substrate, a protease substrate, a killing substrate, and a combination thereof.

3. The hydrogel of claim 1, wherein the biocompatibility substrate is selected from the group consisting of: a poly(ethylene glycol) (PEG), a poly(vinyl alcohol) (PVA), a poly(acrylic acid) (PAA), a poly(propylene fumarate-co-ethylene glycol) (P(PF-co-EG)), a polyacrylamide, a polypeptide, a poly-N-substituted glycine oligomer (polypeptoid), hyaluronic acid (HA), an alginate, a chitosan, an agarose, a collagen, an elastin, a silk, a fibrin, a gelatin, a dextran, a combination thereof, and a derivative of each of these.

4. The hydrogel of claim 1, wherein the Q substrate is selected from the group consisting of: SEQ ID NOs. 1-5, QQ, QQQ, and a combination thereof.

5. The hydrogel of claim 1, wherein the K substrate is selected from the group consisting of: (SEQ ID NO. 6)$_n$G, (SEQ ID NO. 7)$_n$G, (SEQ ID NO. 8)$_n$G, and a combination thereof, where n is 1 to 600.

6. The hydrogel of claim 1, wherein the random coil substrate is selected from the group consisting of: SEQ ID NOs. 6-8, (SEQ ID NO. 1)$_2$, (SEQ ID NO. 2)$_3$, and a combination thereof.

7. The hydrogel of claim 1, wherein the cancerous human cell is selected from the group consisting of: a prostate cancer cell, a breast cancer cell, a brain cancer cell, an ovarian cancer cell, a bladder cancer cell, a lung cancer cell, and a colon cancer cell.

8. The hydrogel of claim 1, wherein the cancerous human cell is attracted to the bioactive substrate.

9. The hydrogel of claim 1, wherein the cancerous human cell is killed by the bioactive substrate.

10. The hydrogel of claim 1, further comprising a second bioactive substrate, wherein the second bioactive substrate attracts the cancer human cell, wherein the bioactive substrate also traps the cancerous human cell in the hydrogel for a period of time.

11. The hydrogel of claim 1, further comprising a second bioactive substrate, wherein the second bioactive substrate attracts the cancerous human cell, wherein the bioactive substrate is substantially toxic to or kills the cancerous human cell.

12. The hydrogel of claim 11, further comprising a third bioactive substrate, wherein the third bioactive substrate traps the cancerous human cell in the hydrogel for a period of time.

13. The hydrogel of claim 1, wherein the hydrogel has a characteristic of stimulating a non-specific immune response in a human.

14. The hydrogel of claim 1, further comprising or releasing one or more agents selected from the group consisting of: a chemoattractant, a chemotherapeutic, and a combination thereof.

15. The hydrogel of claim 1, wherein one or both of the Q block and the K block include the biocompatibility substrate.

16. The hydrogel of claim 1, wherein the biocompatibility substrate is grafted onto one or both of the Q block and the K block.

17. The hydrogel of claim 2, wherein the attraction substrate is selected from the group consisting of: Insulin-like Growth Factor (IGF-1), osteopontin, osteonectin, Epidermal Growth Factor 1 (EGF-1), Stromal Cell-Derived Factor 1 (SDF-1), bone morphogenetic protein factor 1 (BMP-1), bone morphogenetic protein factor 2 (BMP-2), Colony Stimulating Factor 1 (CSF-1), and a combination thereof.

18. The hydrogel of claim 2, wherein the adhesion substrate is selected from the group consisting of: a peptide containing an RGD amino acid sequence, PHSRN (SEQ ID NO. 14) from fibronectin, KQAGDV (SEQ ID NO. 15) from fibronectin, YIGSR (SEQ ID NO. 16) from elastin, a cadherin protein, and a combination thereof.

19. The hydrogel of claim 1, wherein the biocompatibility substance is selected from the group consisting of: a poly (ethylene glycol) (PEG), a poly(vinyl alcohol) (PVA), a poly (acrylic acid) (PAA), a poly(propylene fumarate-co-ethylene glycol) (P(PF-co-EG)), a polyacrylamide, a polypeptide, a poly-N-substituted glycine oligomer or polymer (polypeptoid), hyaluronic acid (HA), an alginate, a chitosan, an agarose, a collagen, a silk, an elastin, a fibrin, a gelatin, a dextran, a combination thereof, and a derivative of each of these.

20. A hydrogel comprising:
a reaction product including a biocompatibility substrate, wherein the reaction product is formed from a Q block and a K block in the presence of an enzymatic cross-linking agent, wherein a Q block includes a Q substrate including at least one glutamine group and the K block includes a K substrate including at least one lysine group, wherein one or both of the Q block and the K block include a random coil substrate; wherein the Q block and the K block are cross-linked to one another via one or more glutamine groups of the Q block and one or more of the lysine groups of the K block, wherein the reaction product is a random coil polypeptide polymer substrate, wherein the biocompatibility substrate is selected from the group consisting of: a poly(ethylene glycol) (PEG), a poly(vinyl alcohol) (PVA), a poly (acrylic acid) (PAA), a poly(propylene fumarate-co-ethylene glycol) (P(PF-co-EG)), a polyacrylamide, a polypeptide, a poly-N-substituted glycine oligomer or polymer (polypeptoid), hyaluronic acid (HA), an alginate, a chitosan, an agarose, a collagen, a silk, an elastin, a fibrin, a gelatin, a dextran, a combination thereof, and a derivative of each of these; wherein the Q substrate is selected from the group consisting of: SEQ ID NOs. 1-5, QQ, QQQ, and a combination thereof; wherein the K substrate is selected from the group consisting of: (SEQ ID NO. 6)$_n$G, (SEQ ID NO. 7)$_n$G, (SEQ ID NO. 8)$_n$G, and a combination thereof, where n is 1 to 600; and wherein the random coil substrate is selected from the group consisting of: SEQ ID NOs. 6-8, (SEQ ID NO. 1)$_2$, (SEQ ID NO. 2)$_3$, and a combination thereof.

21. The hydrogel of claim 20, wherein the enzymatic cross-linking agent is a transglutaminase enzyme.

22. The hydrogel of claim 21, further comprising: one or both of the Q block and the K block include a bioactive substrate.

23. The hydrogel of claim 22, wherein the bioactive substrate is selected from the group consisting of an adhesion substrate, an attraction substrate, a protease substrate, a killing substrate, and a combination thereof.

24. A random coil polypeptide polymer substrate hydrogel, comprising:
a random coil polypeptide polymer substrate including:
a Q block including a Q substrate including at least one glutamine group;
a K block including a K substrate including at least one lysine group; and
a biocompatibility substrate or a biocompatibility substance,
wherein the Q block and the K block are crosslinked to one another via one or more glutamine groups of the Q block and one or more of the lysine groups of the K block;
wherein one or both of the Q block and the K block include a random coil protein substrate.

25. The hydrogel of claim 24, further comprising: one or both of the Q block and the K block include a bioactive substrate, wherein the bioactive substrate is selected from the group consisting of an adhesion substrate, an attraction substrate, a protease substrate, a killing substrate, and a combination thereof.

26. The hydrogel of claim 25, wherein a cancerous human cell has an affinity for the bioactive substrate.

27. The hydrogel of claim 26, further comprising a second bioactive substrate, wherein the second bioactive substrate attracts the cancer human cell, wherein the bioactive substrate also traps the cancerous human cell in the hydrogel for a period of time.

28. The hydrogel of claim 26, further comprising a second bioactive substrate, wherein the second bioactive substrate attracts the cancerous human cell, wherein the bioactive substrate is substantially toxic to or kills the cancerous human cell.

29. The hydrogel of claim 28, further comprising a third bioactive substrate, wherein the third bioactive substrate traps the cancerous human cell in the hydrogel for a period of time.

30. The hydrogel of claim 24, wherein the biocompatibility substrate is selected from the group consisting of: a polyethylene glycol) (PEG), a poly(vinyl alcohol) (PVA), a poly (acrylic acid) (PAA), a poly(propylene fumarate-co-ethylene glycol) (P(PF-co-EG)), a polyacrylamide, a polypeptide, a poly-N-substituted glycine oligomer (polypeptoid), hyaluronic acid (HA), an alginate, a chitosan, an agarose, a collagen, an elastin, a silk, a fibrin, a gelatin, a dextran, a combination thereof, and a derivative of each of these.

31. The hydrogel of claim 24, wherein the Q substrate is selected from the group consisting of: GQQQLGGAGTGSA, GAGQGEA, QQ, QQQ, GLQQQ, LQQQG, GLQQQG and a combination thereof; wherein the K substrate is selected from the group consisting of: (GKGTGA)nG, (GKGSGKGA)nG, (GKAGTGSA)nG, and a combination thereof, where n is 1 to 600; and wherein the random coil substrate is selected from the group consisting of: GKGSGKGA, GKGTGA, GKAGTGSA, (GQQQLGGAGTGSA)2, (GAGQGEA)3, and a combination thereof.

32. The hydrogel of claim 24, further comprising or releasing one or more agents selected from the group consisting of: a chemoattractant, a chemotherapeutic, and a combination thereof.

33. The hydrogel of claim 24, wherein one or both of the Q block and the K block include the biocompatibility substrate.

34. The hydrogel of claim 24, wherein the biocompatibility substrate is grafted onto one or both of the Q block and the K block.

35. The hydrogel of claim 24, wherein the bioactive substrate is the adhesion substrate, wherein the adhesion substrate is selected from the group consisting of: a peptide containing an RGD amino acid sequence, PHSRN from fibronectin, KQAGDV from fibronectin, YIGSR from elastin, a cadherin protein, and a combination thereof.

36. A hydrogel comprising:
a reaction product including a biocompatibility substrate, wherein the reaction product is formed from a Q block and a K block in the presence of an enzymatic cross-linking agent, wherein a Q block includes a Q substrate including at least one glutamine group and the K block includes a K substrate including at least one lysine group, wherein one or both of the Q block and the K block include a random coil substrate;

wherein the Q block and the K block are cross-linked to one another via one or more glutamine groups of the Q block and one or more of the lysine groups of the K block, wherein the reaction product is a random coil polypeptide polymer substrate.

37. The hydrogel of claim 36, wherein the enzymatic cross-linking agent is a transglutaminase enzyme.

38. The hydrogel of claim 36, wherein the biocompatibility substrate is selected from the group consisting of: a poly(ethylene glycol) (PEG), a poly(vinyl alcohol) (PVA), a poly(acrylic acid) (PAA), a poly(propylene fumarate-co-ethylene glycol) (P(PF-co-EG)), a polyacrylamide, a polypeptide, a poly-N-substituted glycine oligomer or polymer (polypeptoid), hyaluronic acid (HA), an alginate, a chitosan, an agarose, a collagen, a silk, an elastin, a fibrin, a gelatin, a dextran, a combination thereof, and a derivative of each of these; wherein the Q substrate is selected from the group consisting of: GQQQLGGAGTGSA, GAGQGEA, QQ, QQQ, GLQQQ, LQQQG, GLQQQG and a combination thereof; wherein the K substrate is selected from the group consisting of: (GKGTGA)nG, (GKGSGKGA)nG, (GKAGTGSA)nG, and a combination thereof, where n is 1 to 600; and wherein the random coil substrate is selected from the group consisting of: GKGSGKGA, GKGTGA, GKAGTGSA, (GQQQLGGAGTGSA)2, (GAGQGEA)3, and a combination thereof.

39. The hydrogel of claim 36, further comprising: one or both of the Q block and the K block include a bioactive substrate, wherein the bioactive substrate is selected from the group consisting of an adhesion substrate, an attraction substrate, a protease substrate, a killing substrate, and a combination thereof.

* * * * *

UNITED STATES PATENT AND TRADEMARK OFFICE
CERTIFICATE OF CORRECTION

PATENT NO. : 8,940,331 B2  
APPLICATION NO. : 12/624043  
DATED : January 27, 2015  
INVENTOR(S) : Annelise E. Barron et al.

It is certified that error appears in the above-identified patent and that said Letters Patent is hereby corrected as shown below:

In the Specification

At column 1, lines 23-27, in the paragraph entitled FEDERAL SPONSORSHIP, delete

"This invention was made, in part, with Government support under Contract/Grant No. 5 R01 EB003806, awarded by the National Institutes of Health, National Institute of Biomedical Imaging and Bioengineering. The Government has certain rights in this invention" and replace with --This invention was made with Government support under contract EB003806 awarded by the National Institutes of Health. The Government has certain rights in the invention--

Signed and Sealed this  
Thirtieth Day of June, 2015

Michelle K. Lee  
*Director of the United States Patent and Trademark Office*